United States Patent [19]

Murugesan et al.

[11] Patent Number: 5,760,038
[45] Date of Patent: Jun. 2, 1998

[54] SUBSTITUTED BIPHENYL SULFONAMIDE ENDOTHELIN ANTAGONISTS

[75] Inventors: Natesan Murugesan, Lawrenceville, N.J.; Joel C. Barrish, Holland, Pa.; Philip D. Stein, Pennington, N.J.

[73] Assignee: Bristol-Myers Squibb Company, Princeton, N.J.

[21] Appl. No.: 384,066

[22] Filed: Feb. 6, 1995

[51] Int. Cl.$^6$ .............. A61K 31/525; A61K 31/505; C07D 405/00; C07D 409/00

[52] U.S. Cl. .............. 514/252; 514/255; 514/256; 514/269; 514/272; 514/274; 514/340; 514/345; 514/348; 514/349; 514/351; 514/352; 514/357; 544/238; 544/405; 544/297; 544/298; 544/310; 544/316; 544/317; 544/319; 544/321; 544/322; 544/324; 544/327; 544/331; 544/333; 546/272.1

[58] Field of Search ............. 548/246; 514/380, 514/252, 255, 256, 269, 272, 274, 357, 340, 352, 345, 351, 348, 349; 544/238, 405, 297, 298, 310, 316, 317, 319, 321, 322, 324, 327, 331, 333; 546/272.1

[56] References Cited

U.S. PATENT DOCUMENTS

| | | | |
|---|---|---|---|
| 2,888,455 | 5/1959 | Kano et al. | 260/239.9 |
| 4,415,496 | 11/1983 | Harris et al. | 260/239.33 |
| 5,236,928 | 8/1993 | Chakravarty et al. | 514/275 |
| 5,270,313 | 12/1993 | Burri et al. | 514/252 |
| 5,292,740 | 3/1994 | Burri et al. | 514/256 |
| 5,378,715 | 1/1995 | Stein et al. | 514/329 |
| 5,464,853 | 11/1995 | Chan et al. | 514/378 |
| 5,514,691 | 5/1996 | Chan et al. | 514/312 |
| 5,571,821 | 11/1996 | Chan et al. | 514/312 |
| 5,591,761 | 1/1997 | Chan et al. | 514/380 |
| 5,594,021 | 1/1997 | Chan et al. | 514/378 |
| 5,612,359 | 3/1997 | Murugesan | 514/365 |

FOREIGN PATENT DOCUMENTS

| | | |
|---|---|---|
| 29589 | 5/1993 | Australia . |
| 34011/93 | 9/1993 | Australia . |
| 67357/94 | 1/1995 | Australia . |
| 48039/96 | 9/1996 | Australia . |
| 76072 | 4/1983 | European Pat. Off. . |
| 194548 | 9/1986 | European Pat. Off. . |
| 404525 | 12/1990 | European Pat. Off. . |
| 443983 | 8/1991 | European Pat. Off. . |
| 510526 | 10/1992 | European Pat. Off. . |
| 526708 | 2/1993 | European Pat. Off. . |
| 601386 | 6/1994 | European Pat. Off. . |
| 617001 | 9/1994 | European Pat. Off. . |
| 626174 | 11/1994 | European Pat. Off. . |
| 633259 | 1/1995 | European Pat. Off. . |
| 634175 | 1/1995 | European Pat. Off. . |
| 640596 | 3/1995 | European Pat. Off. . |
| 682016 | 11/1995 | European Pat. Off. . |
| 702012 | 3/1996 | European Pat. Off. . |
| 749964 | 12/1996 | European Pat. Off. . |
| 1059459 | 6/1959 | Germany . |
| 0364506 | 11/1962 | Switzerland . |
| 804036 | 11/1958 | United Kingdom . |
| 0897440 | 5/1962 | United Kingdom . |
| 1473433 | 5/1977 | United Kingdom . |
| 2228933 | 9/1990 | United Kingdom . |
| 91/15479 | 10/1991 | WIPO . |
| 93/08799 | 5/1993 | WIPO . |
| 93/23404 | 11/1993 | WIPO . |
| 94/27979 | 12/1994 | WIPO . |
| 95/26957 | 10/1995 | WIPO . |
| 96/31492 | 10/1996 | WIPO . |
| 96/40681 | 12/1996 | WIPO . |

OTHER PUBLICATIONS

S. Norio et l., Chemical Abstracts, vol. 70, No. 19, (1969), 87639g.

T. Saito, Chemical Abstracts, vol. 73, No. 23 (1970), 120511w.

Derwent Abstract No. 88–289069/41 Feb. 27, 1987.
Derwent Abstract No. 88–195835/28 Nov. 26, 1986.
Derwent Abstract No. 88–061295/09 Jul. 9, 1986.
Derwent Abstract No. 87–152485/22 Oct. 11, 1985.
Derwent Abstract No. 62299 E/30 Dec. 11, 1980.
Derwent Abstract No. 40927 D/23 Sep. 11, 1979.
Derwent Abstract No. 91–254550/35 Feb. 19, 1990.
Derwent Abstract No. 86–246709/38 Nov. 27, 1985.
Derwent Abstract No. 35012 K/15 Sep. 24, 1981.

Allen et al., "Preparation . . . antagonists", CA116(11):106284Z, p. 778, 1992.

R.D. Desai et al., Chemical Abstracts, vol. 71, No. 11, (1969) 49825c.

R.D. Desai et al., Chemical Abstracts, vol. 71, No. 3, (1969) 12872q.

P. G. Ferrini et al., Angew. Chem. Internat. Edit., vol. 2, No. 2 (1963) p. 99.

A. M. van Leusen, et al., "Synthesis . . . Compounds" J. Org. Chem., vol. 41, 4, (1976), pp. 69–71.

(List continued on next page.)

*Primary Examiner*—Mark L. Berch
*Assistant Examiner*—Bruck Kifle
*Attorney, Agent, or Firm*—Suzanne E. Babajko

[57] ABSTRACT

Compounds of the formula

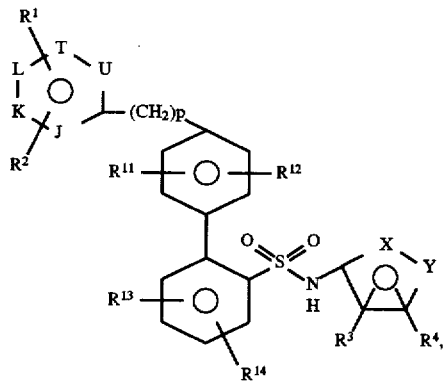

in which the symbols are as defined herein, inhibit the activity of endothelin.

26 Claims, No Drawings

OTHER PUBLICATIONS

W. J. Hammar et al., J. Heterocyclic Chem., vol. 18, (1981) pp. 885–888.

A. M. van Leusen et al., Tetrahedron Letters, No. 23, (1972), pp. 2369–237.

Chan et al., "Identification of a New Class of $ET_A$ Selective Endothelin Antagonists by Pharmacophore Directed Screening", Biochemical and Biophysical Research Communications, vol. 201, No. 1, May 30, 1994, pp. 228–234.

Stein et al., "The Discovery of Sulfonamide Endothelin Antagonists and the Development of the Orally Active $ET_A$ Antagonist 5-(Dimethylamino)-N-(3, 4-dimethyl-5-isoxazolyl)-1-naphthalenesulfonamide", J. Med. Chem., vol. 37, No. 3, Feb. 4, 1994, pp. 329–331.

Doherty, J. Med. Chem., 35(9), 1493–1508 (May 1992).

CA 65: 2241d (1966).

CA 92:41908v (1980).

Wang et al., "Nitrile . . . sinomin," CA 108:94444w, p. 651 (1988).

Khanna, "Oral . . . formulation," CA 115:35728p, p. 415 (1991).

Stein et al., "The Discovery . . . 1-naphthalenesulfonamide," CA 120:18233n, pp. 21–22 (1994).

Vree et al., "Renal excretion . . . function," CA 97:84685r, p. 23 (1982).

Oie, "Pharmacokinetics . . . dosing," CA102:197512x, p. 18 (1985).

Murugesan et al., "N-(heteroaryl) . . . antagonists," CA 120:270370c, p. 1067 (1994).

SUBSTITUTED BIPHENYL SULFONAMIDE ENDOTHELIN ANTAGONISTS

FIELD OF THE INVENTION

This invention relates to endothelin antagonists useful, inter alia, for treatment of hypertension.

BRIEF DESCRIPTION OF THE INVENTION

Compounds of the formula

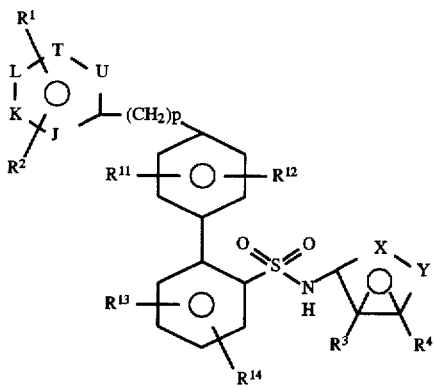

its enantiomers and diastereomers, and pharmaceutically acceptable salts thereof are endothelin receptor antagonists useful, inter alia, as antihypertensive agents. Throughout this specification, the above symbols are defined as follows:

one of X and Y is N and the other is O;

$R^1$ and $R^2$ are each directly bonded to a ring carbon and are each independently
(a) hydrogen;
(b) alkyl or alkoxy;
(c) hydroxyl;
(d) halo; or
(e) amino;

$R^3$ and $R^4$ are each directly bonded to a ring carbon and are each independently
(a) hydrogen;
(b) alkyl, alkenyl, alkynyl, alkoxy, cycloalkyl, cycloalkylalkyl, cycloalkenyl, cycloalkenylalkyl, aryl, aryloxy, aralkyl or aralkoxy, any of which may be substituted with $Z^1$, $Z^2$ and $Z^3$;
(c) halo;
(d) hydroxyl;
(e) cyano;
(f) nitro;
(g) —C(O)H or —C(O) $R^5$;
(h) —$CO_2H$ or —$CO_2R^5$;
(i) —$Z^4$—$NR^6R^7$;
(j) —$Z^4$—$N(R^{10})$—$Z^5$—$NR^8R^9$; or
(k) $R^3$ and $R^4$ together may also be alkylene or alkenylene, either of which may be substituted with $Z^1$, $Z^2$ and $Z^3$, completing a 4- to 8-membered saturated, unsaturated or aromatic ring together with the carbon atoms to which they are attached;

$R^5$ is alkyl, alkenyl, alkynyl, cycloalkyl, cycloalkylalkyl, cycloalkenyl, cycloalkenylalkyl, aryl or aralkyl, any of which may be substituted with $Z^1$, $Z^2$ and $Z^3$;

$R^6$, $R^7$, $R^8$, $R^9$ and $R^{10}$ are each independently
(a) hydrogen; or
(b) alkyl, cycloalkyl, cycloalkylalkyl, cycloalkenylalkyl, aryl or aralkyl, any of which may be substituted with $Z^1$, $Z^2$ and $Z^3$; or $R^6$ and $R^7$ together may be alkylene or alkenylene, either of which may be substituted with $Z^1$, $Z^2$ and $Z^3$, completing a 3- to 8-membered saturated or unsaturated ring together with the nitrogen atom to which they are attached; or any two of $R^8$, $R^9$ and $R^{10}$ together are alkylene or alkenylene, either of which may be substituted with $Z^1$, $Z^2$ and $Z^3$, completing a 3- to 8-membered saturated or unsaturated ring together with the atoms to which they are attached;

$R^{11}$, $R^{12}$, $R^{13}$ and $R^{14}$ are each independently
(a) hydrogen;
(b) alkyl, alkenyl, alkynyl, alkoxy, cycloalkyl, cycloalkylalkyl, cycloalkenyl, cycloalkenylalkyl, aryl, aryloxy, aralkyl or aralkoxy, any of which may be substituted with $Z^1$, $Z^2$ and $Z^3$.
(c) halo;
(d) hydroxyl;
(e) cyano;
(f) nitro;
(g) —C(O)H or —C(O)$R^5$;
(h) —$CO_2H$ or —$CO_2R^5$;
(i) —SH, —$S(O)_nR^5$, —$S(O)_m$—OH, —$S(O)_m$—$OR^5$, —O—$S(O)_m$—$OR^5$, —O—$S(O)_m$OH or —O—$S(O)_m$—$OR^5$;
(j) —$Z^4$—$NR^6R^7$; or
(k) —$Z^4$—$N(R^{10})$—$Z^5$—$NR^8R^9$;

$Z^1$, $Z^2$ and $Z^3$ are each independently
(a) hydrogen;
(b) halo;
(c) hydroxy;
(d) alkyl;
(e) alkenyl;
(f) aralkyl;
(g) alkoxy;
(h) aryloxy;
(i) aralkoxy;
(j) —SH, —$S(O)_nZ^6$, —$S(O)_m$—OH, —$S(O)_m$—$OZ^6$, —O—$S(O)_m$—$Z^6$, —O—$S(O)_m$OH or —O—$S(O)_m$—$OZ^6$;
(k) oxo;
(l) nitro;
(m) cyano;
(n) —C(O)H or —C(O)$Z^6$;
(o) —$CO_2H$ or —$CO_2Z^6$;
(p) —$Z^4$—$NZ^7Z^8$;
(q) —$Z^4$—$N(Z^{11})$—$Z^5$—$Z^6$; or
(r) —$Z^4$—$N(Z^{11})$—$Z^5$—$NZ^7Z^8$;

$Z^4$ and $Z^5$ are each independently
(a) a single bond;
(b) —$Z^9$—$S(O)_n$—$Z^{10}$—;
(c) —$Z^9$—C(O)—$Z^{10}$—;
(d) —$Z^9$—C(S)—$Z^{10}$—;
(e) —$Z^9$—O—$Z^{10}$—;
(f) —$Z^9$—S—$Z^{10}$—; or
(g) —$Z^9$—O—C(O)—$Z^{10}$—;
(h) —$Z^9$—C(O)—O—$Z^{10}$—;

$Z^6$ is alkyl, alkenyl, alkynyl, cycloalkyl, cycloalkylalkyl, cycloalkenyl, cycloalkenylalkyl, aryl or aralkyl;

$Z^7$ and $Z^8$ are each independently hydrogen, alkyl, cycloalkyl, cycloalkylalkyl, cycloalkenylalkyl, aryl or aralkyl, or $Z^7$ and $Z^8$ together are alkylene or alkenylene, completing a 3- to 8-membered saturated or unsaturated ring together with the nitrogen atom to which they are attached;

$Z^9$ and $Z^{10}$ are each independently a single bond, alkylene, alkenylene or alkynylene;

$Z^{11}$ is
  (a) hydrogen; or
  (b) alkyl, cycloalkyl, cycloalkylalkyl, cycloalkenylalkyl, aryl or aralkyl;

or any two of $Z^7$, $Z^8$ and $Z^{11}$ together are alkylene or alkenylene, completing a 3- to 8-membered saturated or unsaturated ring together with the atoms to which they are attached;

J, K, L, T and U are each independently N or C, provided that at least one is N, and at most two are N; and when only one of J, K, L, T and U is N, the N may be substituted with —O$^\ominus$ so that an N-oxide is formed;

each m is independently 1 or 2;

each n is independently 0, 1 or 2; and p is 0 or an integer from 1 to 2.

For compound I, it is preferred that:

$R^1$ and $R^2$ are each independently hydrogen, alkyl or alkoxy;

$R^3$ and $R^4$ are each independently alkyl;

$R^{11}$, $R^{12}$, $R^{13}$ and $R^{14}$ are each hydrogen or substituted alkyl; and p is 0.

Most preferred compounds are those wherein:

$R^1$ and $R^2$ are each independently lower alkoxy or hydrogen; and $R^3$ and $R^4$ are each independently lower alkyl, especially methyl.

DETAILED DESCRIPTION OF THE INVENTION

Listed below are definitions of terms used in this specification. These definitions apply to the terms as used throughout this specification, individually or as part of another group, unless otherwise limited in specific instances.

The term "alkyl" or "alk-" refers to straight or branched chain hydrocarbon groups having 1 to 10 carbon atoms, preferably 1 to 7 carbon atoms. The expression "lower alkyl" refers to alkyl groups of 1 to 4 carbon atoms.

The term "alkoxy" refers to alkyl-O—. The expression "lower alkoxy" refers to lower alkyl-O—.

The term "aryl" or "ar-" refers to phenyl, naphthyl and biphenyl.

The term "alkenyl" refers to straight or branched chain hydrocarbon groups of 2 to 10 carbon atoms having at least one double bond. Groups of two to four carbon atoms are preferred.

The term "alkynyl" refers to straight or branched chain groups of 2 to 10 carbon atoms having at least one triple bond. Groups of two to four carbon atoms are preferred.

The term "alkylene" refers to a straight chain bridge of 1 to 5 carbon atoms connected by single bonds (e.g., —(CH$_2$)$_x$— wherein x is 1 to 5), which may be substituted with 1 to 3 lower alkyl groups.

The term "alkenylene" refers to a straight chain bridge of 2 to 5 carbon atoms having one or two double bonds that is connected by single bonds and may be substituted with 1 to 3 lower alkyl groups. Exemplary alkenylene groups are —CH=CH—CH=CH—, —CH$_2$—CH=CH—, —CH$_2$—CH=CH—CH$_2$—, —C(CH$_3$)$_2$CH=CH— and —CH(C$_2$H$_5$)—CH=CH—.

The term "alkynylene" refers to a straight chain bridge of 2 to 5 carbon atoms that has a triple bond therein, is connected by single bonds, and may be substituted with 1 to 3 lower alkyl groups. Exemplary alkynylene groups are —C≡C—, —CH$_2$—C≡C—, —CH(CH$_3$)—C≡C— and —C≡C—CH(C$_2$H$_5$)CH$_2$—.

The term "alkanoyl" refers to groups of the formula —C(O)alkyl.

The terms "cycloalkyl" and "cycloalkenyl" refer to cyclic hydrocarbon groups of 3 to 8 carbon atoms.

The term "hydroxyalkyl" refers to an alkyl group including one or more hydroxy radicals such as —CH$_2$CH$_2$OH, —CH$_2$CHOHCH$_2$OH, —CH(CH$_2$OH)$_2$ and the like.

The terms "halogen" and "halo" refer to fluorine, chlorine, bromine and iodine.

Throughout the specification, groups and substituents thereof are chosen to provide stable moieties and compounds.

The compounds of formula I form salts which are also within the scope of this invention. Pharmaceutically acceptable (i.e., non-toxic, physiologically acceptable) salts are preferred, although other salts are also useful, e.g., in isolating or purifying the compounds of this invention.

The compounds of formula I may form salts with alkali metals such as sodium, potassium and lithium, with alkaline earth metals such as calcium and magnesium, with organic bases such as dicyclohexylamine, t-butyl amine, benzathine, N-methyl-D-glucamide and hydrabamine, and with amino acids such as arginine, lysine and the like. Such salts may be obtained by reacting compound I with the desired ion in a medium in which the salt precipitates or in an aqueous medium followed by lyophilization.

When the $R^1$ to $R^4$ or $R^{11}$ to $R^{14}$ substituents comprise a basic moiety, such as amino or substituted amino, compound I may form salts with a variety of organic and inorganic acids. Such salts include those formed with hydrochloric acid, hydrogen bromide, methanesulfonic acid, sulfuric acid, acetic acid, maleic acid, benzenesulfonic acid, toluenesulfonic acid and various other sulfonates, nitrates, phosphates, borates, acetates, tartrates, maleates, citrates, succinates, benzoates, ascorbates, salicylates and the like. Such salts may be formed by reacting compound I in an-equivalent amount of the acid in a medium in which the salt precipitates or in an aqueous medium followed by lyophilization.

In addition, when the $R^1$ to $R^4$ or $R^{11}$ to $R^{14}$ substituents comprise a basic moiety such as amino, zwitterions ("inner salts") may be formed.

Certain of the $R^1$ to $R^4$ and $R^{11}$ to $R^{14}$ substituents of compound I may contain asymmetric carbon atoms. Such compounds of formula I may exist, therefore, in enantiomeric and diastereomeric forms and in racemic mixtures thereof. All are within the scope of this invention. Additionally, compound I may exist as enantiomers even in the absence of asymmetric carbons. All such enantiomers are within the scope of this invention.

The compounds of formula I are antagonists of ET-1, ET-2 and/or ET-3 and are useful in treatment of conditions associated with increased ET levels (e.g., dialysis, trauma and surgery) and of all endothelin-dependent disorders. They are thus useful as antihypertensive agents. By the administration of a composition having one (or a combination) of the compounds of this invention, the blood pressure of a hypertensive mammalian (e.g., human) host is reduced. They are also useful in pregnancy-induced hypertension and coma (preeclampsia and eclampsia), acute portal hypertension and hypertension secondary to treatment with erythropoietin.

The compounds of the present invention are also useful in the treatment of disorders related to renal, glomerular and mesangial cell function, including acute and chronic renal failure, glomerular injury, renal damage secondary to old age or related to dialysis, nephrosclerosis (especially hypertensive nephrosclerosis), nephrotoxicity (including nephrotoxicity related to imaging and contrast agents and to cyclosporine), renal ischemia, primary vesicoureteral reflux, glomerulosclerosis and the like. The compounds of this invention may also be useful in the treatment of disorders related to paracrine and endocrine function.

The compounds of the present invention are also useful in the treatment of endotoxemia or endotoxin shock as well as hemorrhagic shock.

The compounds of the present invention are also useful in hypoxic and ischemic disease and as anti-ischemic agents for the treatment of, for example, cardiac, renal and cerebral ischemia and reperfusion (such as that occurring following cardiopulmonary bypass surgery), coronary and cerebral vasospasm, and the like.

In addition, the compounds of this invention may also be useful as anti-arrhythmic agents; anti-anginal agents; antifibrillatory agents; anti-asthmatic agents; anti-atherosclerotic and anti-arteriosclerotic agents; additives to cardioplegic solutions for cardiopulmonary bypasses; adjuncts to thrombolytic therapy; and anti-diarrheal agents. The compounds of this invention may be useful in therapy for myocardial infarction; therapy for peripheral vascular disease (e.g., Raynaud's disease and Takayashu's disease); treatment of cardiac hypertrophy (e.g., hypertrophic cardiomyopathy); treatment of primary pulmonary hypertension (e.g., plexogenic, embolic) in adults and in the newborn and pulmonary hypertension secondary to heart failure, radiation and chemotherapeutic injury, or other trauma; treatment of central nervous system vascular disorders, such as stroke, migraine and subarachnoid hemorrhage; treatment of central nervous system behavioral disorders; treatment of gastrointestinal diseases such as ulcerative colitis, Crohn's disease, gastric mucosal damage, ulcer and ischemic bowel disease; treatment of gall bladder or bile duct-based diseases such as cholangitis; treatment of pancreatitis; regulation of cell growth; treatment of benign prostatic hypertrophy; restenosis following angioplasty or following any procedures including transplantation; therapy for congestive heart failure including inhibition of fibrosis; inhibition of left ventricular dilatation, remodeling and dysfunction; and treatment of hepatotoxicity and sudden death. The compounds of this invention may be useful in the treatment of sickle cell disease including the initiation and/or evolution of the pain crises of this disease; treatment of the deleterious consequences of ET-producing tumors such as hypertension resulting from hemangiopericytoma; treatment of early and advanced liver disease and injury including attendant complications (e.g., hepatotoxicity, fibrosis and cirrhosis); treatment of spastic diseases of the urinary tract and/or bladder; treatment of hepatorenal syndrome; treatment of immunological diseases involving vasculitis such as lupus, systemic sclerosis, mixed cryoglobulinemia; and treatment of fibrosis associated with renal dysfunction and hepatotoxicity. The compounds of this invention may be useful in therapy for metabolic and neurological disorders; cancer; insulin-dependent and non insulin-dependent diabetes mellitus; neuropathy; retinopathy; maternal respiratory distress syndrome; dysmenorrhea; epilepsy; hemorrhagic and ischemic stroke; bone remodeling; psoriasis; and chronic inflammatory diseases such as rheumatoid arthritis, steoarthritis, sarcoidosis and eczematous dermatitis (all types of dermatitis).

The compounds of this invention can also be formulated in combination with endothelin converting enzyme (ECE) inhibitors, such as phosphoramidon; thromboxane receptor antagonists; potassium channel openers; thrombin inhibitors (e.g., hirudin and the like); growth factor inhibitors such as modulators of PDGF activity; platelet activating factor (PAF) antagonists; angiotensin II (AII) receptor antagonists; renin inhibitors; angiotensin converting enzyme (ACE) inhibitors such as captopril, zofenopril, fosinopril, ceranapril, alacepril, enalapril, delapril, pentopril, quinapril, ramipril, lisinopril and salts of such compounds; neutral endopeptidase (NEP) inhibitors; dual NEP-ACE inhibitors; HMG CoA reductase inhibitors such as pravastatin and mevacor; squalene synthetase inhibitors; bile acid sequestrants such as questran; calcium channel blockers; potassium channel activators; beta-adrenergic agents; antiarrhythmic agents; diuretics, such as chlorothiazide, hydrochlorothiazide, flumethiazide, hydroflumethiazide, bendroflumethiazide, methylchlorothiazide, trichloromethiazide, polythiazide or benzothiazide as well as ethacrynic acid, tricrynafen, chlorthalidone, furosemide, musolimine, bumetanide, triamterene, amiloride and spironolactone and salts-of such compounds; and thrombolytic agents such as tissue plasminogen activator (tPA), recombinant tPA, streptokinase, urokinase, prourokinase and anisoylated plasminogen streptokinase activator complex (APSAC). If formulated as a fixed dose, such combination products employ the compounds of this invention within the dosage range described below and-the other pharmaceutically active agent within its approved dosage range. The compounds of this invention may also be formulated with, or useful in conjunction with, antifungal and immunosuppressive agents such as amphotericin B, cyclosporins and the like to counteract the glomerular contraction and nephrotoxicity secondary to such compounds. The compounds of this invention may also be used in conjunction with hemodialysis.

The compounds of the invention can be administered orally or parenterally to various mammalian species known to be subject to such maladies, e.g., humans, in an effective amount within the dosage range of about 0.1 to about 100 mg/kg, preferably about 0.2 to about 50 mg/kg and more preferably about 0.5 to about 25 mg/kg (or from about 1 to about 2500 mg, preferably from about 5 to about 2000 mg) in single or 2 to 4 divided daily doses.

The active substance can be utilized in a composition such as tablet, capsule, solution or suspension containing about 5 to about 500 mg per unit dosage of a compound or mixture of compounds of formula I or in topical form for wound healing (0.01 to 5% by weight compound of formula I, 1 to 5 treatments per day). They may be compounded in a conventional manner with a physiologically acceptable vehicle or carrier, excipient, binder, preservative, stabilizer, flavor, etc., or with a topical carrier such as Plastibase (mineral oil gelled with polyethylene) as called for by accepted pharmaceutical practice.

The compounds of the invention may also be administered topically to treat peripheral vascular diseases and as such may be formulated as a cream or ointment.

The compounds of formula I can also be formulated in compositions such as sterile solutions or suspensions for parenteral administration. About 0.1 to 500 milligrams of a compound of formula I is compounded with a physiologically acceptable vehicle, carrier, excipient, binder, preservative, stabilizer, etc., in a unit dosage form as called for by accepted pharmaceutical practice. The amount of active substance in these compositions or preparations is such that a suitable dosage in the range indicated is obtained.

The compounds of the present invention may be prepared as follows.

SCHEME I

A.

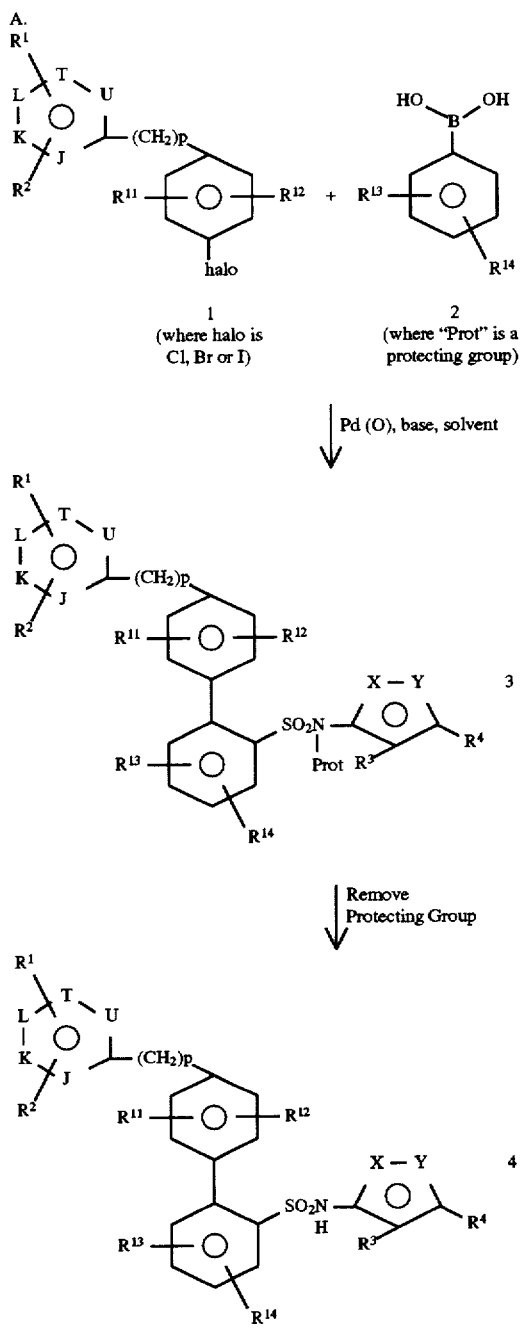

1
(where halo is Cl, Br or I)

2
(where "Prot" is a protecting group)

Pd (O), base, solvent

Remove Protecting Group

As depicted above by Scheme I, the title compounds 4 may be prepared by a Pd(O) catalyzed coupling of an appropriately protected phenylsulfonamide-2-boronic acid intermediate 2, with a 4-heterocyclic aryl halide 1. The coupling is performed in the presence of a suitable base, such as aqueous potassium carbonate, and a solvent, such as a mixture of toluene and ethanol. The resulting compound 3 is converted into the title compound 4 by removal of the protecting group.

If the boronic acid group of intermediate 2 is replaced by a trialkyltin moiety, then intermediate 2 may also be coupled to compound 1 where —OSO$_2$CF$_3$ replaces the halo group.

A boronic acid intermediate 2 shown in scheme I may be prepared from a 2-bromophenylsulfonamide 5 (preparation of which is described in EP Publication number 0,569,193 (1993)) as shown below in Scheme II by lithiation with a suitable alkyl lithium (such as n-butyl lithium), subsequent treatment with a trialkylborate (e.g., triisopropyl borate) and finally adding an aqueous acid such as aqueous hydrochloric acid:

SCHEME II

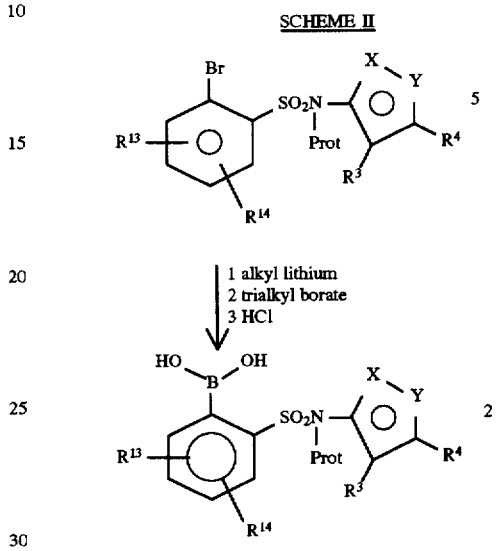

1 alkyl lithium
2 trialkyl borate
3 HCl (In the schemes shown herein, "Prot" is an appropriate protecting group for the sulfonamide function. This is also described in EP Publication number 0,569,193 (1993).)

B. The title compounds may also be prepared by alternate routes shown below in SCHEMES III and IV:

SCHEME III

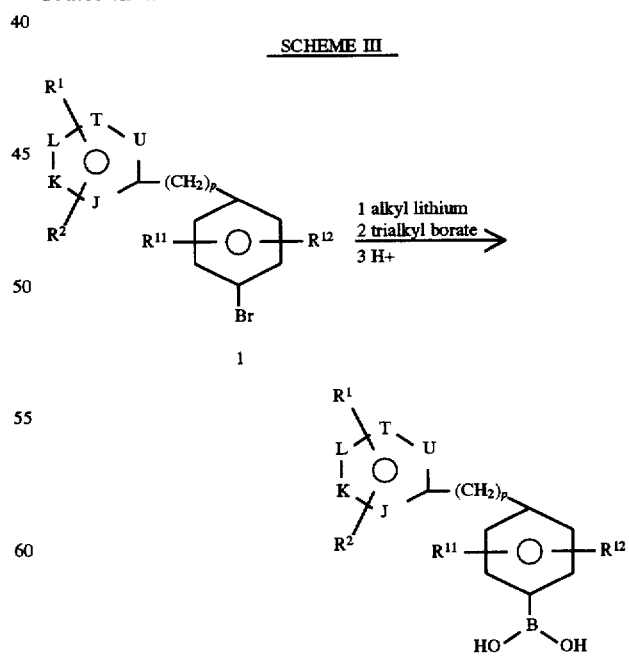

1 alkyl lithium
2 trialkyl borate
3 H+

-continued
SCHEME III

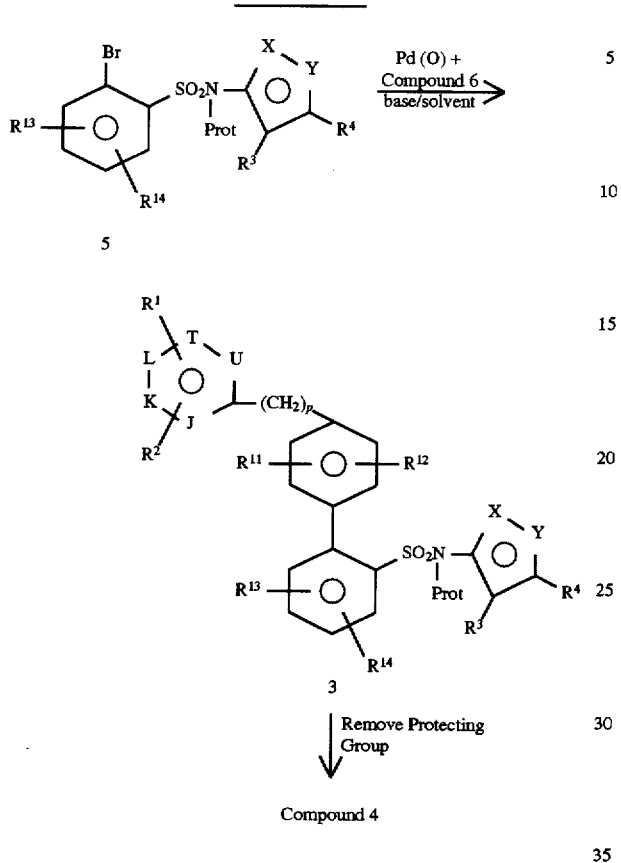

As depicted above in Scheme III, a 4'-Heterocyclic aryl halide 1 can be converted to a boronic acid intermediate 6 via the sequence shown. This compound 6, upon Pd(O) catalyzed coupling with a compound 5, provides a biaryl analog 3. Upon deprotection, biaryl analog 3 leads to the title compound 4. If the boronic acid group of compound 6 is replaced by a trialkyltin moiety, then compound 6 may also be coupled to compound 5 when —$OSO_2CF_3$ replaces the halo group.

SCHEME IV

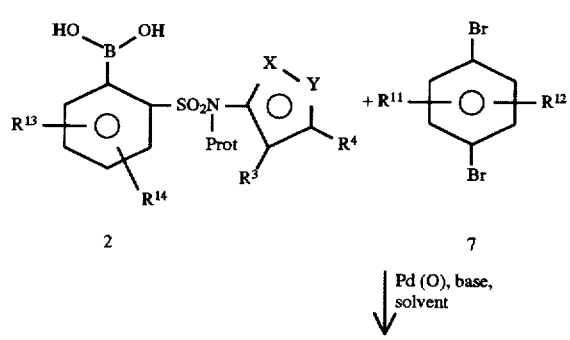

-continued
SCHEME IV

As shown in Scheme IV, the title compound 4' can be prepared by the Pd(O) catalyzed coupling of the boronic acid derivative 2, with a 1,4-dibromobenzene 7 to provide the 4'-bromo-biphenyl derivative 8. Pd(O) coupling of compound 8 with either a heterocyclic boronic acid or a heterocyclic tin derivative (where $R^{15}$ is lower alkyl) then affords, after deprotection, the title compound 4'.

(For general strategies in biaryl synthesis, see, e.g., Bringmann, et al., *Angew. Chem. Int.*, Ed. Engl. 22 (1990) 977–991. For heterocycles, see, e.g., V. N. Kalinin, Synth. 413–432 (1992) and T. R. Bailey, Tetrahedron Lett. 27, (1986) 4407–4410.)

C. The 41'-heterocyclic aryl halide 1 can be prepared by those skilled in the art by a variety of methods described in the literature. A few representative examples are shown below:

SCHEME V i.)

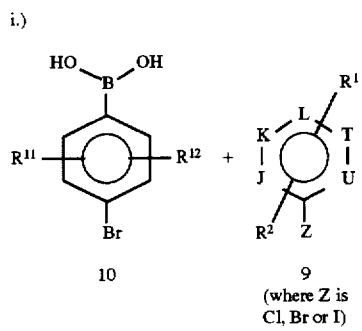

10

9
(where Z is Cl, Br or I)

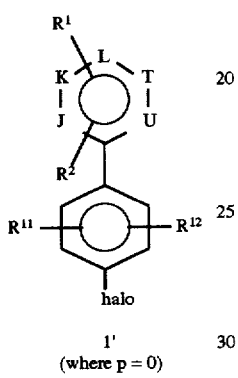

1'
(where p = 0)

As shown in Scheme V, the Pd(O) catalyzed cross-coupling of a 4-bromo phenylboronic acid (10) with a heterocyclic halide 9, in the presence of a base and suitable solvents, provides the 41'-heterocyclic aryl halide 1'. A variety of 41'-heterocycles such as pyridines and pyrimidines can be prepared using this method. See, for example, Mitchell and Wallbank, Tet. Lett., 32, 2273 (1991).

SCHEME VI ii.)

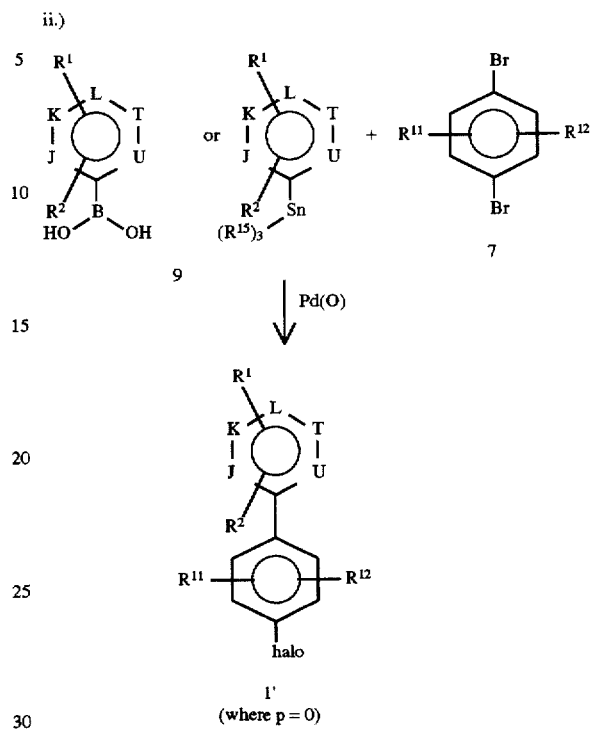

1'
(where p = 0)

As shown, a heterocyclic boronic acid or related tin species (9) can be coupled with a 1,4-dibromobenzene 7 in the presence of Pd(O) to provide a 4'-heterocyclic aryl halide 1' (where p=0).

Compounds, shown by formula 9 are either commercialy available or can be prepared by methods known in the art. See "The Chemistry of Heterocyclic Compounds", John Wiley & Sons.

In certain instances, the boronic acid may be replaced with a tin species to perform the coupling reaction. (Again, for general strategies in biaryl synthesis, see: Bringmann et al., *Angew. Chem. Int., Ed. Engl.* 22 (1990) 977–991.)

D. The 4'-alkyl pyridine or pyrimidine title compounds may also be prepared by the alternate route shown below in Scheme VII. In these compounds, K, L and T are C, at least one of J and U is N, and p is 1 or 2:

SCHEME VII

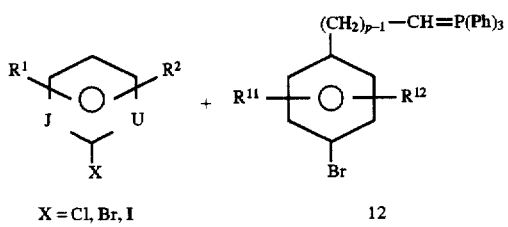

X = Cl, Br, I

11

12

↙ ↙
↙ OH⁻

-continued
SCHEME VII

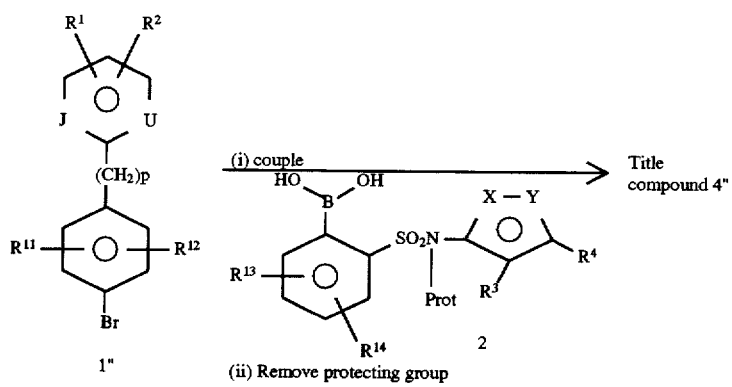

As shown, the treatment of a 2-halo pyridine or a 2-halopyrimidine 11 with a Wittig ylide 12, prepared by methods known in the art, followed by hydrolysis of the intermediate using an aqueous base such as sodium carbonate, provides the corresponding 4-bromophenylalkyl pyridine/pyrimidine 1". Pd(O) catalyzed cross-coupling of 1" with 2, followed by removal of the protecting group, affords the title compund 4". (See, for example, E. C. Taylor and S. F. Martin, J Am. Chem. Soc., 94, (1972) 2874.)

E. A typical example for forming an N-oxide is shown below in Scheme VIII:

SCHEME VIII

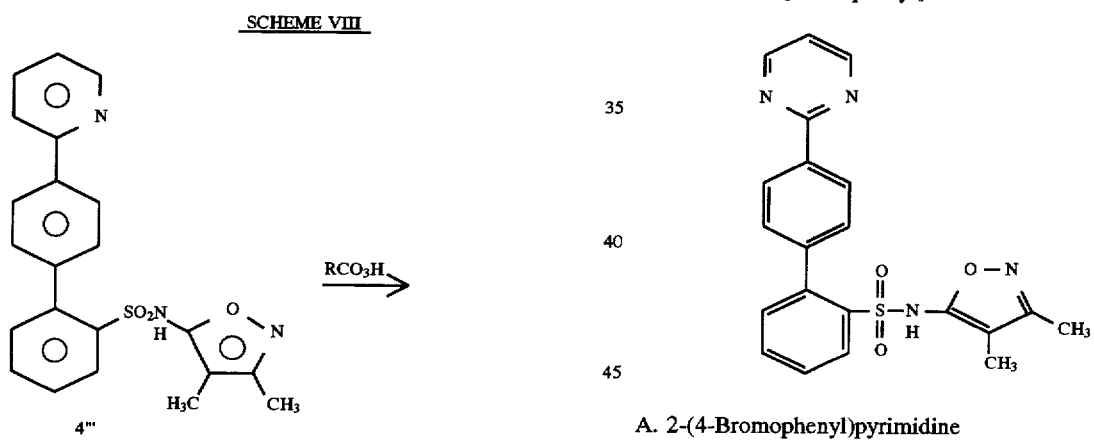

R = CH$_3$, m-chlorophenyl, etc.

The appropriate pyridine analogs can be oxidized to the corresponding N-oxide derivatives using a variety of known oxidizing agents such as m-chloroperbenzoic acid or peracetic acid. The above scheme is also applicable to other isomeric pyridine analogs.

The invention will now be further described by the following working examples, which are preferred embodiments of the invention. These examples are meant to be illustrative rather than limiting.

EXAMPLE 1

N-(3,4-Dimethyl-5-isooxazolyl)-4'-(2-pyrimidinyl) [1,1'-biphenyl]-2-sulfonamide

A. 2-(4-Bromophenyl)pyrimidine

To a solution of 0.8 g (4.0 mmol) of p-bromo phenylboronic acid and 0.23 g (0.2 mmol) of tetrakis (triphenylphosphine)palladium(0) in 20 mL of toluene under argon, 10 mL of 2M aqueous sodium carbonate was added, followed by 1.0 g (6.23 mmol) of 2-bromopyrimidine in 10 mL of 95% ethanol. The mixture was refluxed for 1.5 hours, diluted with 100 mL of water and extracted with 3×50 mL of ethyl acetate. The combined organic extracts were washed once with 100 mL of brine, dried and evaporated. The residue was chromatographed on 100 g of silica gel using hexanes/ethyl acetate 3:1 to afford 0.82 g of compound A as a white solid.

B. N-(3,4-Dimethyl-5-isoxazolyl)-N-[(2-methoxyethoxy) methyl]-4'-(2-pyrimidinyl)[1,1'-biphenyl]-2-sulfonamide To a solution of 0.35 g (0.91 mmol) of 2-Borono-N-(3, 4-dimethyl-5-isoxazolyl)-N-[(2-methoxyethoxy)methyl] benzenesulfonamide and 0.052 g (0.045 mmol) of tetrakis (triphenylphosphine)palladium(0) in 20 mL of toluene under argon, 10 mL of 2M aqueous sodium carbonate was added followed by 0.278 g (1.18 mmol) of compound A in 10 mL of 95% ethanol. The mixture was refluxed for 1.5 hours, diluted with 100 mL of water and extracted with 3×50 mL of ethyl acetate. The combined organic extracts were washed once with 100 mL of brine, dried and evaporated. The residue was chromatographed on 75 g of silica gel using hexanes/ethyl acetate 2:1 to afford 0.14 g (39%) of compound B as a colorless gum.

C. N-(3,4-Dimethyl-5-isoxazolyl)-4'-(2-pyrimidinyl)[1,1'-biphenyl]-2-sulfonamide To a solution of 0.13 g (0.25 mmol) of compound B in 6 mL of 95% ethanol, 6 mL of 6N aqueous hydrochloric acid was added and refluxed for 1.5 hours. The mixture was then concentrated and diluted with 10 mL of water, and the solution was neutralized to pH 7 using aqueous sodium bicarbonate. The mixture was then reacidified to pH 4 using glacial acetic acid, and the solution was extracted with 3×50 mL of ethyl acetate. The combined organic extracts were washed once with water, dried and evaporated (0.11 g). This material was purified by reverse phase preparative HPLC on a 30×500 mm ODS S10 column using 70% solvent B (90% methanol, 10% water, 0.1% trifluoroacetic acid) and 30% solvent A (10% methanol, 90% water, 0.1% trifluoroacetic acid). The appropriate fractions were collected and neutralized with aqueous sodium bicarbonate to pH 7 and concentrated to 10 mL. The solution was then acidified to pH 4 using glacial acetic acid and the white solid was filtered and dried to provide 0.09 g (87%) of the title compound. M.p. >210° C.

$^1$H NMR(CDCl$_3$): δ 1.70 (s, 3H), 2.00 (s, 3H), 6.49 (br s, 1H), 7.09–8.70 (m, 10H).

$^{13}$C NMR (CDCl$_3$): δ 6.6, 10.8, 108.5, 119.4, 127.3, 127.8, 128.0, 129.0, 130.3, 132.5, 133.1, 137.4, 138.0, 140.7, 141.0, 154.1, 157.3, 161.8, 164.1.

EXAMPLE 2

N-(3,4-Dimethyl-5-isoxazolyl)-4'-(2-pyridinyl)[1,1'-biphenyl]-2-sulfonamide

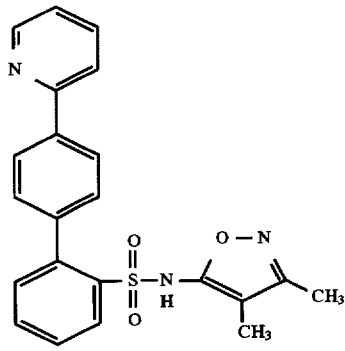

A. 2-(4-Bromophenyl)pyridine

To a solution of 2.0 g (9.96 mmol) of p-bromo phenylboronic acid and 0.57 g (0.5 mmol) of tetrakis (triphenylphosphine)palladium(0) in 20 mL of toluene under argon, 15 mL of 2M aqueous sodium carbonate was added followed by 3.16 g (20 mmol) of 2-bromopyridine in 15 mL of 95% ethanol. The mixture was refluxed for 2 hours, diluted with 100 mL of water and extracted with 3×50 mL of ethyl acetate. The combined organic extracts were washed once with 100 mL of brine, dried and evaporated. The residue was chromatographed on 100 g of silica gel using hexanes/ethyl acetate 4:1 to afford 2.3 g of compound A as a light yellow solid which solidified on standing.

B. N-(3,4-Dimethyl-5-isoxazolyl)-N-[(2-methoxyethoxy)methyl]-4'-(2-pyridinyl)[1,1'-biphenyl]-2-sulfonamide To a solution of 1.47 g (3.84 mmol) of 2-Borono-N-(3,4-dimethyl-5-isoxazolyl)-N-[(2-methoxyethoxy)methyl]benzenesulfonamide and 0.173 g (0.15 mmol) of tetrakis (triphenylphosphine)palladium(0) in 40 mL of toluene under argon, 20 mL of 2M aqueous sodium carbonate was added, followed by 1.0 g (4.27 mmol) of compound A in 20 mL of 95% ethanol. The mixture was refluxed for 2 hours, diluted with 100 mL of water and extracted with 3×50 mL of ethyl acetate. The combined organic extracts were washed once with 100 mL of brine, dried and evaporated. The residue was chromatographed on 50 g of silica gel using hexanes/ethyl acetate 2:1 to afford 0.91 g (47%) of compound B as a colorless gum.

C. N-(3,4-Dimethyl-5-isoxazolyl)-4'-(2-pyridinyl)[1,1'-biphenyl]-2-sulfonamide

To a solution of 0.9 g (1.78 mmol) of compound B in 12 mL of 95% ethanol, 12 mL of 6N aqueous hydrochloric was added and the mixture was refluxed for 2 hours. The mixture was then concentrated and diluted with 25 mL of water and the solution was neutralized to pH 7 using aqueous sodium bicarbonate. The mixture was acidified to pH 4 using glacial acetic acid, and the solution was then extracted with 3×50 mL of ethyl acetate. The combined organic extracts were washed once with water, dried and evaporated (0.75 g). The residue was chromatographed on 25 g of silica gel using hexanes/ethyl acetate 3:2 to provide 0.53 g (73%) of the title compound. M.p. 85°–90° C.

Analysis calculated for C$_{22}$H$_{19}$N$_3$O$_3$S. 1.17 H$_2$O: Calculated: C, 61.94; H, 5.04; N, 9.85; S, 7.52. Found: C, 62.10; H, 4.66; N, 9.69; S, 7.81.

EXAMPLE 3

N-(3,4-Dimethyl-5-isoxazolyl)-4'-(3-pyridinyl)[1,1'-biphenyl]-2-sulfonamide

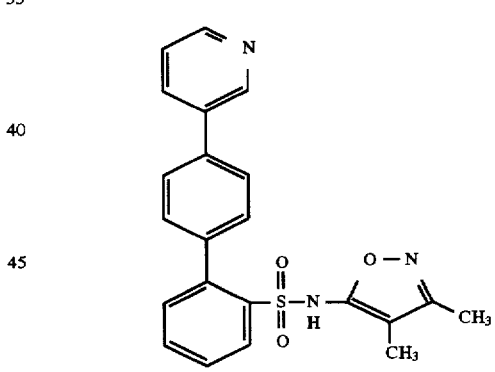

A. 3(4-Bromophenyl)pyridine

To a solution of 4-bromophenylboronic acid (1.41 g, 7 mmol), 3-bromopyridine (6.64 g, 42 mmol) in 50 mL of toluene and 40 mL of 95% ethanol under argon, tetrakis (triphenylphosphine)palladium(0) (809 mg, 0.7 mmol) was added, followed by 30 mL of 2M aqueous sodium carbonate. The reaction mixture was heated at 8500 for 1.5 hours, cooled and diluted with 150 mL of ethyl acetate. The organic liquid was separated and washed with 20 mL water and 20 mL brine, dried and concentrated. The residue was chromatographed on silica gel using 4:1 hexane/ethyl acetate to afford compound A (1.5 g, 92%) as a colorless oil.

B. N-(3,4-Dimethyl-5-isoxazolyl)-N-[(2-methoxyethoxy) methyl]-4'-(3-pyridinyl)[1,1'-biphenyl]-2-sulfonamide To a solution of 2-Borono-N-(3,4-dimethyl-5-isoxazolyl)-N-[(2-methoxyethoxy)methyl]benzenesulfonamide (384 mg, 1.0 mmol), compound A (351 mg, 1.5 mmol) in 9 mL of toluene and 7.2 mL of 95% ethanol under argon, tetrakis (triphenylphosphine)palladium(0) (116 mg, 0.1 mmol) was added followed by 5.4 mL of 2M aqueous sodium carbonate. The reaction mixture was heated at 75° C. for 3 hours, cooled and diluted with 50 ml of ethyl acetate. The organic liquid was separated and washed with 10 mL water and 10 mL brine, dried and concentrated. The residue was chromatographed on silica gel using 1:2 hexane/ethyl acetate to afford compound B (346 mg, 70%) as a colorless gum.

C. N-(3,4-Dimethyl-5-isoxazolyl)-4'-(3-pyridinyl)[1,1'-biphenyl]-2-sulfonamide

To a solution of compound B (346 mg, 0.70 mmol) in 10 mL of 95% ethanol, 10 mL of 6N aqueous hydrochloric acid was added and refluxed for 1 hour. The reaction mixture was concentrated and the pH of the solution was adjusted to 8 using sodium bicarbonate solution. It was then reacidified to pH 5 with glacial acetic acid. The mixture was extracted with 3×40 mL ethyl acetate. The organic liquid was washed with 10 mL water and 10 mL brine, dried and concentrated. The residue as chromatographed on silica gel using 100:2.5 dichloromethane/methanol to afford the title compound (199 mg, 70%) as a white solid. M.p. 96°–106° C. (amorphous).

Analysis calculated for $C_{22}H_{19}N_3O_3S \cdot 0.44\ H_2O$: Calculated: C, 63.92; H, 4.83; N, 10.17; S, 7.76. Found: C, 63.95; H, 4.64; N, 10.14; S, 7.55.

EXAMPLE 4

4'-(4,6-Dimethoxy-2-pyrimidinyl)-N-(3,4-dimethyl-5-isoxazolyl)[1,1'-biphenyl]-2-sulfonamide

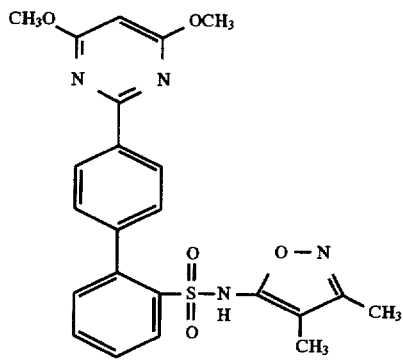

A. 2-Chloro-4,6-dimethoxypyrimidine

To a solution of 2-amino-4,6-dimethoxypyrimidine (12.41 g, 80 mmol) in 66 mL of concentrated hydrochloric acid at −8° to −12° C., a solution of sodium nitrite (11.04 g, 160 mmol) in 22 mL water was added over 30 minutes. The mixture was stirred at room temperature overnight. The precipitate was separated by filtration and washed with small amount of water. The solid was dissolved in 200 mL dichloromethane, dried (magnesium sulfate) and filtered, and the filtrate was concentrated to give compound A (3.74 g, 27%) as a white solid.

B. 2-(4-Bromophenyl)-4,6-dimethoxypyrimidine

To a solution of 4-bromophenylboronic acid (602 mg, 3 mmol), compound A (524 mg, 3 mmol) in 22.5 mL of toluene and 18 mL of 95% ethanol under argon, tetrakis (triphenylphosphine)palladium(0) (208 mg, 0.18 mmol) was added, followed by 13.5 mL of 2M aqueous sodium carbonate. The reaction mixture was-heated at 80° C. for 1.25 hours, cooled and diluted with 60 mL of ethyl acetate. The organic liquid was separated and washed with 15 mL water and 15 mL brine, dried and concentrated. The residue was chromatographed on silica gel using 4:1 hexane/dichloromethane to afford compound B (170 mg, 19%) as a white solid.

C. 4'-(4,6-Dimethoxy-2-pyrimidinyl)-N-(3,4-dimethyl-5-isoxazolyl)-N-[(2-methoxyethoxy)methyl][1,1'-biphenyl]-2-sulfonamide To a solution of 2-Borono-N-(3,4-dimethyl-5-isoxazolyl)-N-[(2-methoxyethoxy)methyl]benzenesulfonamide (384 mg, 1.0 mmol), compound B (339 mg, 1.15 mmol) in 9 mL of toluene and 7.2 mL of 95% ethanol under argon, tetrakis (triphenylphosphine)palladium(0) (116 mg, 0.1 mmol) was added, followed by 5.4 mL of 2M aqueous sodium carbonate. The reaction mixture was heated at 75° C. for 3 hours, cooled and diluted with 50 mL of ethyl acetate. The organic liquid was separated, washed with 10 mL water and 10 mL brine, dried and concentrated. The residue was chromatographed on silica gel using 3:1 hexane/ethyl acetate to afford compound C (370 mg, 67%) as a colorless gum.

D. 4'-(4,6-Dimethoxy-2-pyrimidinyl)-N-(3,4-dimethyl-5-isoxazolyl)[1,1'-biphenyl]-2-sulfonamide To a solution of compound C (370 mg, 0.67 mmol) in 15 mL of 95% ethanol, 15 mL of 6N aqueous hydrochloric acid was added and refluxed for 45 minutes. The reaction mixture was concentrated and the pH of the solution was adjusted to 8 using sodium bicarbonate solution. It was then acidified to pH 5 with glacial acetic acid. The mixture was extracted with 3×50 mL ethyl acetate. The organic liquid was washed with 15 mL water and 15 mL brine, dried and concentrated. The residue was chromatographed on silica gel using 10:1 and then 5:1 dichloromethane/ethyl acetate to afford the title compound (185 mg, 60%) as a white solid. M.p. 83°–93° C. (amorphous).

Analysis calculated for $C_{23}H_{22}N_4O_5S$: Calculated: C, 59.22; H, 4.75; N, 12.01; S, 6.87. Found: C, 59.15; H, 4.76; N, 11.73; S, 6.56.

EXAMPLE 5

N-(3,4-Dimethyl-5-isoxazolyl)-4'-(4-pyrimidinyl)[1'-biphenyl]-2-sulfonamide

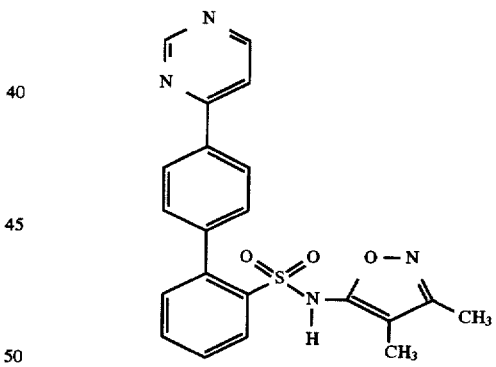

A. 4-(4-Bromophenyl)pyrimidine n-Butyllithium (1.6M in hexanes, 8.0 mL, 13 mmol) was added dropwise over 8 minutes to a solution of 1,4-dibromobenzene (3.6 g, 15 mmol) in ether (22 mL) stirring at 0° C. under argon in an oven-dried flask. After stirring at 0° C. for 30 minutes, the reaction solution was cooled to −35° C. and a solution of pyrimidine (1.2 g, 1.2 mL, 15 mmol) in ether (15 mL) was added over 10 minutes. After stirring at −35° C. for 20 minutes, the reaction was quenched with water (4.5 mL) and transferred to a separatory funnel. Extraction with ether (2×30 ml) and dichloromethane (30 mL), and drying the combined organic layers over magnesium sulfate, afforded 4.2 g of material after evaporation of the solvent.

The residue was dissolved in acetone and saturated acetone solution of potassium permagnate (~30 mL) was added until the purple color remained. This solution was refluxed for 10 minutes. The reaction was filtered through Celite®, rinsing with acetone and ethanol, and the filtrate was evaporated to afford 2.3 g of crude product. Recrystallization from heptane afforded 0.78 g (24%) of compound A. M.p. 81.0°–83.5° C.

B. N-(3,4-Dimethyl-5-isoxazolyl)-N-[(2-methoxyethoxy)methyl]-4'-(4-pyrimidinyl)[1,1'-biphenyl]-2-sulfonamide A solution of 2-Borono-N-(3,4-dimethyl-5-isoxazolyl)-N-[(2-methoxyethoxy)methyl]benzenesulfonamide (1.0 g, 1.6 mmol) in ethanol (sparged with argon 20 minutes, 7.2 mL) was added to a solution of compound A (0.50 g, 2.0 mmol) in toluene (sparged with argon 20 minutes, 14 mL). To this solution was added a solution of sodium carbonate (0.45 g) in water (sparged with argon 20 minutes, 7.2 mL) followed by tetrakis(triphenylphosphine)palladium(0) (0.13 g, 0.11 mmol). After refluxing under argon for 4.5 hours, the solution was cooled and poured into brine (20 mL). Extraction with ethyl acetate (2×70 mL) and drying the combined organic layers over magnesium sulfate afforded 1.6 g of crude product after evaporation of the solvent. Flash chromatography (silica, 50 mm diameter, 50% ethyl acetate/dichloromethane) afforded 0.20 g (25%) of compound B.

C. N-(3,4-Dimethyl-5-isoxazolyl)-4'-(4-pyrimidinyl)[1,1'-biphenyl]-2-sulfonamide A solution of compound B (0.20 g, 0.40 mmol) in ethanol (6.0 mL) and 6N hydrochloric acid (6.0 mL) was stirred at 80° C. After 7 hours, the ethanol was evaporated in vacuo, and the residue transferred to a separatory funnel with dichloromethane/water. The aqueous layer was brought to pH 1.5 with saturated sodium bicarbonate. Extraction with dichloromethane (4×20 mL) and drying over magnesium sulfate afforded 0.24 g of crude product after evaporation of the solvent. Flash chromatography (silica, 15 mm diameter, 8% methanol/dichloromethane) followed by recrystallization from hot methanol afforded 42 mg (26%) of the title compound. M.p. =211.0°–214.0° C.

Analysis calculated for $C_{21}H_{18}N_4O_3S \cdot 0.16\ H_2O$: Calculated: C, 61.61; H, 4.51; N, 13.68; S, 7.83. Found: C, 61.66; H, 4.42; N, 13.63; S, 7.60.

EXAMPLE 6

N-(3,4-Dimethyl-5-isoxazolyl)-4'-(2-pyrazinyl)[1,1'-biphenyl]-2-sulfonamide

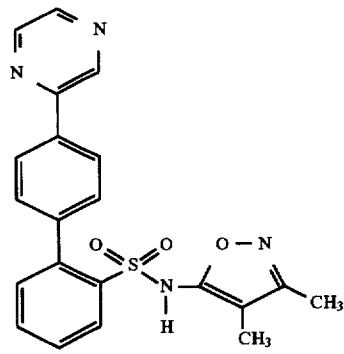

A. 2-(4-Bromophenyl)pyrazine n-Butyllithium (1.6M in hexanes, 8.0 mL, 13 mmol) was added dropwise over 8 minutes to a solution of 1,4-dibromobenzene (3.6 g, 15 mmol) in ether (22 mL) stirring at 0° C. under argon in an oven-dried flask. After stirring at 0° C. for 30 minutes, this solution was added over 13 minutes to a solution of pyrazine (0.86 g, 11 mmol, 0.86 mL) in tetrahydrofuran (34 mL) stirring at –78° C. Once the addition was complete, dry air (passed through a bed of calcium sulfate) was bubbled through the solution. After 30 minutes, the cold bath was removed, and then after another 30 minutes, the reaction was quenched with water (4.5 mL) and transferred to a separatory funnel. Extraction with dichloromethane (2×50 mL) and drying the combined organic layers over magnesium sulfate afforded 3.9 g of material after evaporation of the solvent. Flash chromatography (silica, 75 mm diameter, 5% ethyl acetate/dichloromethane) afforded 0.93 g (36%) of compound A. M.p. 105.0°–107.5° C.

B. N-(3,4-Dimethyl-5-isoxazolyl)-N-[(2-methoxyethoxy)methyl]-4'-(2-pyrazinyl)[1,1'-biphenyl]-2-sulfonamide A solution of 2-Borono-N-(3,4-dimethyl-5-isoxazolyl)-N-[(2-methoxyethoxy)methyl]benzenesulfonamide (1.0 g, 1.6 mmol) in ethanol (sparged with argon 20 minutes, 7.2 mL) was added to a solution of compound A (0.50 g, 2.0 mmol) in toluene (sparged with argon 20 minutes, 14 mL). To this solution was added a solution of sodium carbonate (0.45 g) in water (sparged with argon 20 minutes, 7.2 mL) followed by tetrakis(triphenylphosphine)palladium(0) (0.13 g, 0.11 mmol). After refluxing under argon for 4 hours, the solution was cooled and poured into brine (20 mL). Extraction with ethyl acetate (2×70 ml) and drying the combined organic layers over magnesium sulfate afforded 1.6 g of crude product after evaporation of the solvent. Flash chromatography (silica, 50 mm diameter, 50% ethyl acetate/dichloromethane) afforded 0.15 g (19%) of compound B.

C. N-(3,4-Dimethyl-5-isoxazolyl)-4'-(2-pyrazinyl)[1,1'-biphenyl]-2-sulfonamide

A solution of compound B (0.15 g, 0.30 mmol) in ethanol (4.6 mL) and 6N hydrochloric acid (4.6 mL) was stirred at 90° C. After 3 hours, the ethanol was evaporated in vacuo, and the residue transferred to a separatory funnel with dichloromethane/water. The aqueous layer was brought to pH 1.5 with saturated sodium bicarbonate. Extraction with dichloromethane (4×20 mL) and drying over magnesium sulfate afforded 0.18 g of crude product after evaporation of the solvent. Flash chromatography (silica, 15 mm diameter, 7% methanol/dichloromethane) afforded 94 mg of almost pure product. Preparative HPLC (YMC S-10, 30×500 mm, 68.4% methanol in water with 1% trifluoroacetic acid, 25 mL/minute, fractions 17 to 19.5 minutes) afforded 64 mg (52%) of the title compound. M.p.=131.0°–134.0° C. Analysis calculated for $C_{21}H_{18}N_4O_3S \cdot 0.50\ H_2O$: Calculated: C, 60.71; H, 4.61; N, 13.49; S, 7.72. Found: C, 60.49; H, 4.37; N, 13.17; S, 8.09.

EXAMPLE 7

N-(3,4-Dimethyl-5-isoxazolyl)-4'-(5-pyrimidinyl)[1,1'-biphenyl]-2-sulfonamide

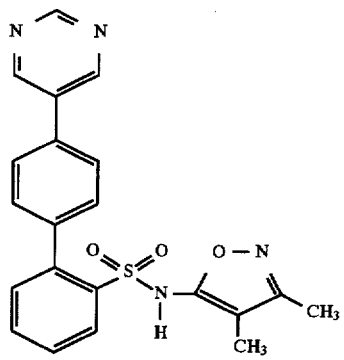

A. 5-(4-Bromophenyl)pyrimidine

A solution of 4-bromophenylboronic acid (2.0 g, 10 mmol) in ethanol (sparged with argon 30 minutes, 44 mL) was added to a solution of 5-bromopyrimidine (1.9 g, 12 mmol) in toluene (sparged with argon 30 minutes, 87 mL). To this solution was added a solution of sodium carbonate (2.7 g) in water (sparged with argon 30 minutes, 44 mL) followed by tetrakis(triphenylphosphine)palladium(0) (0.76 g, 0.66 mmol). After stirring under argon at 75° C. for 1 hour, the solution was cooled and poured into brine (50 mL). Extraction with ethyl acetate (2×250 mL) and drying the combined organic layers over magnesium sulfate afforded 3.4 g of crude product after evaporation of the solvent. Flash chromatography (silica, 50 mm diameter, 5% to 10% ethyl acetate/dichloromethane) followed by recrystallization from hot ether afforded 1.0 g (42%) of compound A. M.p. 144.0°–146.5° C.

B. N-(3,4-Dimethyl-5-isoxazolyl)-N-[(2-methoxyethoxy)methyl]-4'-(5-pyrimidinyl)[1,1'-biphenyl]-2-sulfonamide A solution of 2-Borono-N-(3,4-dimethyl-5-isoxazolyl)-N-[(2-methoxyethoxy)methyl]benzenesulfonamide (1.0 g, 1.6 mmol) in ethanol (sparged with argon 20 minutes, 7.2 mL) was added to a solution of compound A (0.50 g, 2.0 mmol) in toluene (sparged with argon 20 minutes, 14 mL). To this solution was added a solution of sodium carbonate (0.45 g) in water (sparged with argon 20 minutes, 7.2 mL) followed by tetrakis(triphenylphosphine)palladium(0) (0.13 g, 0.11 mmol). After stirring at 75° C. under argon for 4 hours, the solution was cooled and poured into brine (20 mL). Extraction with ethyl acetate (2×70 mL) and drying the combined organic layers over magnesium sulfate afforded 1.8 g of crude product after evaporation of the solvent. Flash chromatography (silica, 50 mm diameter, 50% ethyl acetate/hexane followed by 10% methanol/ethyl acetate) afforded 0.15 g (19%) of compound B.

C. N-(3,4-Dimethyl-5-isoxazolyl)-4'-(5-pyrimidinyl)[1,1'-biphenyl]-2-sulfonamide A solution of compound B (0.15 g, 0.30 mmol) in ethanol (4.6 mL) and 6N hydrochloric acid (4.6 mL) was stirred at 90° C. After 2 hours, the ethanol was evaporated in vacuo, and the residue was transferred to a separatory funnel with dichloromethane/water. The aqueous layer was brought to pH 2.0 with saturated sodium bicarbonate. Extraction with dichloromethane (4×20 mL) and drying over magnesium sulfate afforded 0.13 g of crude product after evaporation of the solvent. Flash chromatography (silica, 15 mm diameter, 7% methanol/dichloromethane) afforded 54 mg of almost pure product. Preparative HPLC (YMC S-10, 30×500 mm, 66.8% methanol in water with 1% trifluoroacetic acid, 25 mL/minute, fractions 16 to 18.7 minutes) afforded 25 mg (20%) of the title compound. M.p. =105.0°–109.0° C.

Analysis Calculated for $C_{21}H_{18}N_4O_3S \cdot 0.40\ C_2HF_3O_2 \cdot 0.90\ H_2O$: Calculated: C, 55.91; H, 4.35; N, 11.96; S, 6.85. Found: C, 55.92; H, 3.97; N, 11.61; S, 7.29.

EXAMPLE 8

N-(3,4-Dimethyl-5-isoxazolyl)-4'-(2-pyridinyl)[1,1'-biphenyl]-2-sulfonamide, $N^{4'}$-oxide

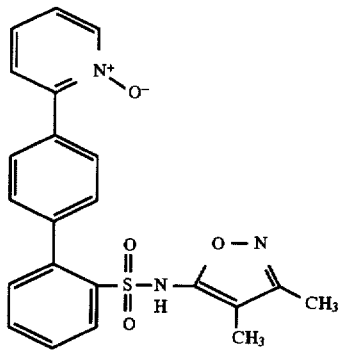

A. N-(3,4-Dimethyl-5-isoxazolyl)-4'-(2-pyridinyl)[1,1'-biphenyl]-2-sulfonamide, $N^{4'}$-oxide To a solution of 0.15 g (0.37 mmol) of the title compound of Example 2, above, in 5 mL of dichloromethane, 0.088 g of m-chloroperbenzoic acid was added and the mixture was stirred at room temperature for 3 hours. The mixture was then evaporated and the residue was purified by reverse phase preparative HPLC on a 30×500 mm ODS S10 column using 58% solvent B (90% methanol, 10% water, 0.1% trifluoroacetic acid) and 42% solvent A (10% methanol, 90% water, 0.1% trifluoroacetic acid). The appropriate fractions were collected, neutralized with aqueous sodium bicarbonate to pH 7 and concentrated to 10 mL. The solution was then acidified to pH 4 using glacial acetic acid and the white solid was filtered and dried to provide 0.088 g (56%) of the title compound. M.p. 110°–117° C.

Analysis Calculated for $C_{22}H_{19}N_3O_4S \cdot 1.70\ H_2O$: Calculated: C, 58.44; H, 4.99; N, 9.29; S, 7.09. Found: C, 58.82; H, 4.36; N, 8.91; S, 6.75.

EXAMPLE 9

N-(3,4-Dimethyl-5-isoxazolyl)-4'-(6-methoxy-2-pyridinyl)[1,1'-biphenyl]-2-sulfonamide

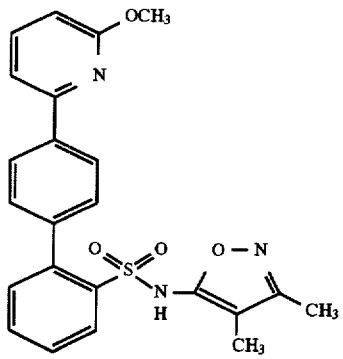

A. 4-Bromo-6-methoxypyridine

A solution of 5.0 g (21.24 mmol) of 2,6-dibromopyridine and 8.2 mL (35.875 mmol) of 25% sodium methoxide/ methanol in 15 mL of methanol was stirred at reflux for about 26 hours at which point TLC (1:1 ethyl acetate:hexane) showed no 2.6-dibromopyridine remaining. The reaction mixture was cooled to room temperature, poured into cold 5% sodium bicarbonate and extracted with ethyl ether. After evaporation, the residue was dissolved in ethyl ether, washed with brine, dried (magnesium sulfate) and evaporated to dryness to give 3.6 g (90%) of a colorless oil.

B. 2-(4-Bromophenyl)-6-methoxypyridine

To 1.88 g (10 mmol) of compound A and 0.5 g (2.5 mmol) of 4-bromophenyl boronic acid in a mixture of 20 mL of degassed toluene and 16 mL of degassed ethanol, was added 0.175 g (0.15 mmol) of tetrakis(triphenylphosphine) palladium(0) and 12 mL of degassed 2N aqueous sodium carbonate. The mixture was stirred at 75° C. for 3 hours. The reaction mixture was cooled to room temperature, diluted with 200 mL of ethyl acetate, washed with water and then brine, dried (magnesium sulfate) and evaporated. Flash chromatography (50 mm×6"; 25% to 50% ethyl acetate/ hexane) gave 1.86 g of a mixture of starting material and product which was chromatographed two additional times (50 mm×6"1; 1% ethyl acetate/hexane, then 50 mm×7"; 0.75% ethyl acetate/hexane) to afford 230 mg (35%) of a colorless oil along with mixed fractions.

C. N-(3,4-Dimethyl-5-isoxazolyl)-N-[(2-methoxyethoxy) methyl]-4'-(6-methoxy-2-pyridinyl)[1,1'-biphenyl]-2-sulfonamide To 230 mg (0.87 mmol) of compound B, and 280 mg (0.73 mmol) of 2-Borono-N-(3,4-dimethyl-5-isoxazolyl)-N-[(2-methoxyethoxy)methyl]benzenesulfonamide in a mixture of 5.5 mL of degassed toluene and 3.7 mL of degassed ethanol, was added 84 mg (0.072 mmol) of tetrakis (triphenylphosphine) palladium(0) and 3.2 mL of degassed 2N aqueous sodium carbonate. The mixture was stirred at 85° C. for 3 hours. The reaction mixture was cooled to room temperature, diluted with ethyl acetate, washed with water and then brine, dried (magnesium sulfate) and evaporated. Flash chromatography (50 mm×6"; 30% to 40% to 50% ethyl acetate/hexane) afforded 172 mg of an oily-solid residue (45%).

D. N-(3,4-Dimethyl-5-isoxazolyl)-4'-(6-methoxy-2-pyridinyl)[1,1'-biphenyl]-2-sulfonamide A mixture of 170 mg (0.325 mmol) of compound C and 7.5 mL of 6N hydrochloric acid in 7.5 mL of ethanol was stirred at 75° C for 30 minutes. Additional water was added. The pH was brought to about 8 with saturated sodium bicarbonate and then brought back to about 4.5 with acetic acid. The mixture was extracted with 3×50 mL ethyl acetate and the organic extracts were washed with 25 mL each of water and brine, dried (magnesium sulfate) and evaporated. Flash chromatography (25 mm×6"; 40% to 50% ethyl acetate/hexane) gave 50 mg of a semi-solid product which was partially purified by trituration with hexane to give 15 mg of the title compound as a white solid. 120 mg of recovered compound C was also isolated and resubmitted to the above reaction conditions (4 mL each of 6N hydrochloric acid and ethanol). After work-up as above, the crude product was combined with the mother liquors from the above trituration and purified by flash chromatography (2×25 mm×8"1; 40% to 50% ethyl acetate/Hexane) to give an additional 50 mg of the title compound as a white solid (65 mg total; 46% yield). M.p. 132°–34° C.

Analysis calculated for $C_{23}H_{21}N_3O_4S \cdot 0.39 H_2O$: Calculated: C, 62.42; H, 4.96; N, 9.49; S, 7.24. Found: C, 62.70; H, 4.87; N, 9.21; S, 6.93.

What is claimed is:

1. A compound of the formula

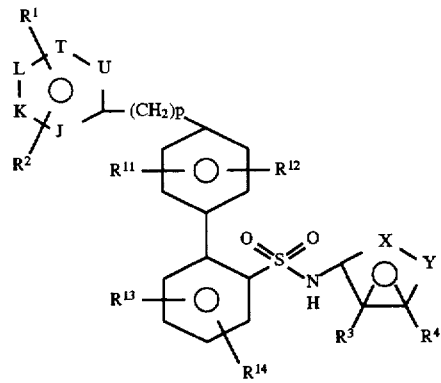

or an enantiomer, diastereomer or pharmaceutically acceptable salt thereof, wherein:
one of X and Y is N and the other is O;
$R^1$ and $R^2$ are each directly bonded to a ring carbon and are each independently
  (a) hydrogen;
  (b) alkyl or alkoxy;
  (c) hydroxyl;
  (d) halo; or
  (e) amino;
$R^3$ and $R^4$ are each directly bonded to a ring carbon and are each independently
  (a) hydrogen;
  (b) alkyl, alkenyl, alkynyl, alkoxy, cycloalkyl, cycloalkylalkyl, cycloalkenyl, cycloalkenylalkyl, aryl, aryloxy, aralkyl or aralkoxy, any of which may be substituted with $Z^1$, $Z^2$ and $Z^3$;
  (c) halo;
  (d) hydroxyl;
  (e) cyano;
  (f) nitro;
  (g) —C(O)H or —C(O) $R^5$;
  (h) —$CO_2H$ or —$CO_2R^5$;
  (i) —$Z^4$—$NR^6R^7$; or
  (j) —$Z^4$—$N(R^{10})$—$Z^5$—$NR^8R^9$; or
  (k) $R^3$ and $R^4$ together may also be alkylene or alkenylene, either of which may be substituted with $Z^1$, $Z^2$ and $Z^3$, completing a 4- to 8-membered saturated, unsaturated or aromatic ring together with the carbon atoms to which they are attached;
$R^5$ is alkyl, alkenyl, alkynyl, cycloalkyl, cycloalkylalkyl, cycloalkenyl, cycloalkenylalkyl, aryl or aralkyl, any of which may be substituted with $Z^1$, $Z^2$ and $Z^3$;
$R^6$, $R^7$, $R^8$, $R^9$ and $R^{10}$ are each independently
  (a) hydrogen; or
  (b) alkyl, cycloalkyl, cycloalkylalkyl, cycloalkenylalkyl, aryl or aralkyl, any of which may be substituted with $Z^1$, $Z^2$ and $Z^3$; or
$R^6$ and $R^7$ together may be alkylene or alkenylene, either of which may be substituted with $Z^1$, $Z^2$ and $Z^3$, completing a 3- to 8-membered saturated or unsaturated ring together with the nitrogen atom to which they are attached; or any two of $R^8$, $R^9$ and $R^{10}$ together are alkylene or alkenylene, either of which may be substituted with $Z^1$, $Z^2$ and $Z^3$, completing a 3- to 8-membered saturated or unsaturated ring together with the atoms to which they are attached;
$R^{11}$, $R^{12}$, $R^{13}$ and $R^{14}$ are each independently (a) hydrogen;
(b) alkyl, alkenyl, alkynyl, alkoxy, cycloalkyl, cycloalkylalkyl, cycloalkenyl, cycloalkenylalkyl, aryl, aryloxy, aralkyl or aralkoxy, any of which may be substituted with $Z^1$, $Z^2$ and $Z^3$;
(c) halo;
(d) hydroxyl;
(e) cyano;
(f) nitro;
(g) —C(O)H or —C(O) $R^5$;
(h) —$CO_2H$ or —$CO_2R^5$;
(i) —SH, —S(O)$_n R^5$, —S(O)$_m$—OH, —S(O)$_m$—$OR^5$, —O—S(O)$_m$—$OR^5$, —O—S(O)$_m$OH or —O—S(O)$_m$—$OR^5$;
(j) —$Z^4$—$NR^6R^7$; or
(k) —$Z^4$—N($R^{10}$)—$Z^5$—$NR^8R^9$;

$Z^1$, $Z^2$ and $Z^3$ are each independently
(a) hydrogen;
(b) halo;
(c) hydroxy;
(d) alkyl;
(e) alkenyl;
(f) aralkyl;
(g) alkoxy;
(h) aryloxy;
(i) aralkoxy;
(j) —SH, —S(O)$_n Z^6$, —S(O)$_m$—OH, —S(O)$_m$—$OZ^6$, —O—S(O)$_m Z^6$, —O—S(O)$_m$OH or —O—S(O)$_m$—$OZ^6$;
(k) oxo;
(l) nitro;
(m) cyano;
(n) —C(O)H or —C(O)$Z^6$;
(o) —$CO_2H$ or —$CO_2Z^6$;
(p) —$Z^4$—$NZ^7Z^8$;
(q) —$Z^4$—N($Z^{11}$)—$Z^5$—$Z^6$; or
(r) —$Z^4$—N($Z^{11}$)—$Z^5$—$NZ^7Z^8$;

$Z^4$ and $Z^5$ are each independently
(a) a single bond;
(b) —$Z^9$—S(O)$_n$—$Z^{10}$—;
(c) —$Z^9$—C(O)—$Z^{10}$—;
(d) —$Z^9$—C(S)—$Z^{10}$—;
(e) —$Z^9$—O—$Z^{10}$—;
(f) —$Z^9$—S—$Z^{10}$—;
(g) —$Z^9$—O—C(O)—$Z^{10}$—; or
(h) —$Z^9$—C(O)—O—$Z^{10}$—;

$Z^6$ is alkyl, alkenyl, alkynyl, cycloalkyl, cycloalkylalkyl, cycloalkenyl, cycloalkenylalkyl, aryl or aralkyl;

$Z^7$ and $Z^8$ are each independently hydrogen, alkyl, cycloalkyl, cycloalkylalkyl, cycloalkenylalkyl, aryl or aralkyl or $Z^7$ and $Z^8$ together are alkylene or alkenylene, completing a 3- to 8-membered saturated or unsaturated ring together with the nitrogen atom to which they are attached;

$Z^9$ and $Z^{10}$ are each independently a single bond, alkylene, alkenylene or alkynylene;

$Z^{11}$ is
(a) hydrogen; or
(b) alkyl, cycloalkyl, cycloalkylalkyl, cycloalkenylalkyl, aryl or aralkyl;
or any two of $Z^7$, $Z^8$ and $Z^{11}$ together are alkylene or alkenylene, completing a 3- to 8-membered saturated or unsaturated ring together with the atoms to which they are attached;

J, K, L, T and U are each independently N or C, provided that at least one is N, and at most two are N; and when only one of J, K, L, T and U is N, the N may be substituted with —O⊖ so that an N-oxide is formed;
each m is independently 1 or 2;
each n is independently 0, 1 or 2; and
p is 0 or an integer from 1 to 2.

2. A compound of claim 1, wherein $R^1$ and $R^2$ are each independently hydrogen, alkyl or alkoxy.

3. A compound of claim 1, wherein $R^3$ and $R^4$ are each independently alkyl.

4. A compound of claim 1, wherein $R^1$ and $R^2$ are each independently hydrogen or alkoxy; and $R^3$ and $R^4$ are each independently alkyl.

5. A compound of claim 1, wherein $R^1$ and $R^2$ are each independently hydrogen or lower alkoxy.

6. A compound of claim 1, wherein $R^3$ and $R^4$ are each independently alkyl of 1 to 4 carbon atoms.

7. A compound of claim 1, wherein $R^3$ and $R^4$ are each methyl.

8. A compound of claim 1, wherein $R^1$ and $R^2$ are each independently hydrogen or lower alkoxy; and $R^3$ and $R^4$ are each independently alkyl of 1 to 4 carbon atoms.

9. A compound of claim 1, wherein $R^1$ and $R^2$ are each independently hydrogen or lower alkoxy; and $R^3$ and $R^4$ are each methyl.

10. A compound of claim 1, wherein p is 0.

11. A compound of claim 1, wherein p is 0; $R^1$ and $R^2$ are each independently hydrogen or lower alkoxy; and $R^3$ and $R^4$ are each methyl.

12. A compound of claim 1, wherein $R^1$ and $R^2$ are each independently hydrogen or lower alkoxy; $R^3$ and $R^4$ are each methyl; $R^{11}$, $R^{12}$, $R^{13}$ and $R^{14}$ are each hydrogen; and p is 0.

13. A compound of claim 1, selected from the group consisting of:

N-(3,4-Dimethyl-5-isoxazolyl)-4'-(2-pyrimidinyl)[1,1'-biphenyl]-2-sulfonamide;

N-(3,4-Dimethyl-5-isoxazolyl)-4'-(2-pyridinyl)[1,1'-biphenyl]-2-sulfonamide;

N-(3,4-Dimethyl-5-isoxazolyl)-4'-(3-pyridinyl)[1,1'-biphenyl]-2-sulfonamide;

4'-(4,6-Dimethoxy-2-pyrimidinyl)-N-(3,4-dimethyl-5-isoxazolyl)[1,1'-biphenyl]-2-sulfonamide;

N-(3,4-Dimethyl-5-isoxazolyl)-4'-(4-pyrimidinyl)[1,1'-biphenyl]-2-sulfonamide;

N-(3,4-Dimethyl-5-isoxazolyl)-4'-(2-pyrazinyl)[1,1'-biphenyl]-2-sulfonamide;

N-(3,4-Dimethyl-5-isoxazolyl)-4'-(5-pyrimidinyl)[1,1'-biphenyl]-2-sulfonamide;

N-(3,4-Dimethyl-5-isoxazolyl)-4'-(2-pyridinyl)[1,1'-biphenyl]-2-sulfonamide, $N^4$-oxide; and N-(3,4-Dimethyl-5-isoxazolyl)-4'-(6-methoxy-2-pyridinyl)[1,1'-biphenyl]-2-sulfonamide.

14. A method of treating endothelin-related disorders in a mammal, which comprises administering to said mammal an effective endothelin-related disorder treating amount of a compound of claim 1.

15. A method of treating hypertension, which comprises administering an effective hypertension treating amount of a compound of claim 1.

16. A method of treating pulmonary hypertension, which comprises administering an effective pulmonary hypertension treating amount of a compound of claim 1.

17. A method of treating renal, glomerular or mesangial cell disorders in a mammal, wherein said disorders are endothelin-related, which comprises administering to said mammal an effective renal, glomerular or mesangial cell disorder treating amount of a compound of claim 1.

18. A method of treating endotoxemia, which comprises administering an effective endotoxemia treating amount of a compound of claim 1.

19. A method of treating ischemia, which comprises administering an effective ischemia treating amount of a compound of claim 1.

20. A method of inhibiting cell growth in a mammal, wherein said cell growth is an endothelin-related disorder, which comprises administering to said mammal an effective cell growth inhibiting amount of a compound of claim 1.

21. A method of treating atherosclerosis, which comprises administering an effective atherosclerosis treating amount of a compound of claim 1.

22. A method of treating restenosis, which comprises administering an effective restenosis treating amount of a compound of claim 1.

23. A method of treating subarachnoid hemorrhage, which comprises administering an effective subarachnoid hemorrhage treating amount of a compound of claim 1.

24. A method of treating benign prostatic hypertrophy, which comprises administering a benign prostatic hypertrophy treating amount of a compound of claim 1.

25. A compound of claim 1 which is N-(3,4-dimethyl-5-isoxazolyl)-4'-(2-pyrimidinyl)[1,1'-biphenyl]-2-sulfonamide.

26. A method of treating congestive heart failure, which comprises administering a congestive heart failure treating amount of a compound of claim 1.

* * * * *